(12) United States Patent
Maddah et al.

(10) Patent No.: US 11,808,760 B1
(45) Date of Patent: Nov. 7, 2023

(54) SYSTEM AND METHODS FOR IN VITRO STRUCTURAL TOXICITY TESTING

(71) Applicant: CURI BIO, INC., Seattle, WA (US)

(72) Inventors: Seyyedeh Mahnaz Maddah, Los Altos, CA (US); Kevin Edward Loewke, Redwood City, CA (US)

(73) Assignee: CURI BIO, INC., Seattle, WA (US)

( * ) Notice: Subject to any disclaimer, the term of this patent is extended or adjusted under 35 U.S.C. 154(b) by 34 days.

(21) Appl. No.: 16/791,896

(22) Filed: Feb. 14, 2020

Related U.S. Application Data

(60) Provisional application No. 62/805,427, filed on Feb. 14, 2019.

(51) Int. Cl.
| | |
|---|---|
| *G01N 33/00* | (2006.01) |
| *G01N 33/50* | (2006.01) |
| *G06T 7/00* | (2017.01) |
| *G06N 3/08* | (2023.01) |
| *G06N 20/00* | (2019.01) |
| *G06F 18/21* | (2023.01) |
| *G06F 18/2431* | (2023.01) |

(52) U.S. Cl.
CPC ....... *G01N 33/5014* (2013.01); *G01N 33/5026* (2013.01); *G06F 18/217* (2023.01); *G06F 18/2431* (2023.01); *G06N 3/08* (2013.01); *G06N 20/00* (2019.01); *G06T 7/0016* (2013.01); *G06T 2207/20081* (2013.01); *G06T 2207/20084* (2013.01); *G06T 2207/30024* (2013.01)

(58) Field of Classification Search
CPC ............ G01N 33/5014; G01N 33/5026; G06N 20/00; G06F 18/217; G06F 18/2431; G06N 3/08; G06T 7/0016; G06T 2207/20081; G06T 2207/20084; G06T 2207/30024

See application file for complete search history.

(56) References Cited

U.S. PATENT DOCUMENTS

| | | | | |
|---|---|---|---|---|
| 2004/0229210 | A1* | 11/2004 | Sabry et al. | C12M 41/46 435/6.16 |
| 2012/0219204 | A1* | 8/2012 | Hong et al. | G01N 33/5067 382/133 |
| 2014/0297199 | A1* | 10/2014 | Osten | G01N 33/5008 435/7.1 |
| 2020/0126234 | A1* | 4/2020 | Yokota et al. | G06T 7/174 |
| 2020/0342597 | A1* | 10/2020 | Chukka et al. | G06V 10/82 |
| 2021/0117729 | A1* | 4/2021 | Bharti et al. | G01N 15/1429 |
| 2021/0372994 | A1* | 12/2021 | Metzger et al. | G01N 33/5014 |

FOREIGN PATENT DOCUMENTS

| | | | | |
|---|---|---|---|---|
| CA | 3052266 | A1* | 8/2018 | A61L 2/0047 |
| EP | 3805401 | A1* | 4/2021 | G01N 33/5008 |

* cited by examiner

Primary Examiner — Khai M Nguyen
(74) Attorney, Agent, or Firm — IPkey PLLC (57) ABSTRACT

A system and process use artificial intelligence to evaluate the toxicity of drugs on cells. In some embodiments, a convolutional neural network is trained to identify features in cells and thereafter identify when structural changes in cells are signs of damage from exposure to a drug. Some embodiments use a 2-class deep neural network, comparing drug-treated cells to controls, to learn which images may show signs of toxicity as a result of the drug. In some applications, the system may capture images from a time-lapse experiment to determine from the cell cultures how a drug affects a cell type over time.

16 Claims, 9 Drawing Sheets

SYSTEM AND METHODS FOR IN VITRO STRUCTURAL TOXICITY TESTING

CROSS-REFERENCE TO RELATED APPLICATIONS

This application claims benefit under 35 U.S.C. § 119(e) of U.S. Provisional Application having Ser. No. 62/805,427 filed Feb. 14, 2019, which is hereby incorporated by reference herein in its entirety.

BACKGROUND

The embodiments herein relate generally to in vitro structural toxicity testing systems.

There is increasing interest in using in vitro models, such as functional cells differentiated from human induced pluripotent stem cells (iPSCs), for drug toxicity testing. Such cells have shown physiologically relevant drug responses that may predict adverse clinical drug effects. One of the key aspects for successful utilization of these cells is the development of accurate phenotypic assays for measuring drug response. Examples of common phenotypic assays include cytotoxicity (e.g. measuring ATP content or nuclear count), or functional toxicity (e.g. looking at contraction profiles of iPSC-derived cardiomyocytes for cardiotoxicity).

There is a need in the field for new and more sensitive types of structural toxicity assays, which may ultimately be able to better predict in vivo clinical toxicity.

SUMMARY

According to one embodiment of the subject technology, a computer program product to determine a response of a cell to a drug is disclosed. The computer program product comprises a non-transitory computer readable storage medium having computer readable program code embodied therewith. The computer readable program code is configured, when executed by a processor, to: receive images of treated cells, wherein treated cells are exposed to the drug, at an initial point in time; receive images of control cells not exposed to the drug, at an initial point in time; forward the images of the treated cells and the images of the control cells to a convolutional neural network; determine by the convolutional neural network whether the images of the treated cells are different from the images of the control cells; and calculating a metric based on the determination by the convolutional neural network.

According to another embodiment, a method for determining a response of a cell to a drug is disclosed. The method comprises: receiving images of treated cells, wherein treated cells are exposed to the drug, at an initial point in time; receiving images of control cells not exposed to the drug, at an initial point in time; forwarding the images of the treated cells and the images of the control cells to a convolutional neural network; determining by the convolutional neural network whether the images of the treated cells are different from the images of the control cells; and calculating a metric based on the determination by the convolutional neural network quantifying an amount of change caused by the drug on the images of the treated cells.

BRIEF DESCRIPTION OF THE FIGURES

The detailed description of some embodiments of the present invention is made below with reference to the accompanying figures, wherein like numerals represent corresponding parts of the figures.

DETAILED DESCRIPTION OF CERTAIN EMBODIMENTS

The word "exemplary" is used herein to mean "serving as an example or illustration." Any aspect or design described herein as "exemplary" is not necessarily to be construed as preferred or advantageous over other aspects or designs.

Generally, embodiments of the subject technology provide systems and methods for using artificial intelligence (AI), such as deep convolutional neural networks (CNNs), to capture drug-induced structural changes from the images of cell cultures. The input is a collection of microscopy images captured and grouped at multiple doses and/or time-points for drug(s) of interest. Some embodiments may include one or more reference sets of images where no drug is applied. For example, a series of 2-class CNN trainings may be performed using embodiments of the system, comparing each test condition to a reference. The output is a set of classification results (for example, classification accuracies or z-factors) that quantify the degree of structural changes that have occurred at each drug, dose, and/or time-point of interest. In embodiments, a series of 2-class convolutional neural network trainings may be performed, where a separate 2-class neural network may be trained for each test condition compared to controls. The series of 2-class convolutional neural network trainings may also be referred to as a series of convolutional neural networks.

The AI aspects of the subject technology are an unconventional feature in determining structural changes to cells as a result of drugs being applied to the cells. Generally, in vitro phenotypic assays may be performed by an individual studying images of the subject cells under test. The subject cells have arbitrary shapes. The effects a drug has on the shape of each cell may be difficult to quantify at any one point in time, especially under the subjective perspective of the individual. However, by integrating the AI aspects of the subject technology to in vitro phenotypic assays, the system may objectively capture the structural changes in cells using training techniques and classification of several samples of cells. Accordingly, the impact of drug effects on cells are repeatably quantifiable and the overall screening of drugs for use on human tissue may be sped up significantly.

As will be appreciated, some aspects of the subject technology include: (1) being able to capture subtle structure changes that occur prior to the onset of noticeable cellular damage or death, potentially detecting drug toxicity with improved sensitivity compared to other assays; (2) being applicable to a variety of cell types that are relevant to structural toxicity, as well as a variety of stains for cellular structures and proteins, and (3) there is no need to define the phenotype a priori, as this approach learns how to model phenotypic differences directly from images.

In common microscopy-based assays, the user decides which image features to measure based on a predetermined expectation or visualization. As will be further appreciated, aspects of the subject technology use a completely unbiased approach, by applying deep learning to the images of cells under observation, which provides more accuracy than humans in image interpretation. In an exemplary embodiment, a deep convolutional neural network learns to distinguish two sets of images grouped by their class labels. The two sets of images are images of drug-treated cells and images of control cells with vehicle-only, and the task of the neural network is to determine if the drug-treated cells appear different from the controls (and if so, by how much). During the training, the neural network learns how to distinguish images from each class, without any visual features being explicitly fed to the network. The network learns a combination of low-level features, such as edges, lines, and colors, and then uses those to progressively learn higher-level features such as shapes, textures, and patterns. The performance of the trained network may then be determined by having it blindly classify images from a validation set. The validation accuracy indicates whether the network has been able to learn a discriminatory feature vector to correctly classify images as either class, e.g. drug-treated or control.

In the application of structural toxicity testing with in vitro cell models, the subject technology addresses problems that stem from the following hurdle: given a set of images of cells treated with different drug concentrations, how does one apply deep learning to quantify the structural changes. One option would be to train a single, multi-class neural network, where the class labels are the different doses of drugs (for example, cells given 6 doses of a drug plus vehicle would result in a 7-class neural network). The challenge of such an approach is that the phenotypes are unbalanced, as some classes exhibit strong phenotypes such as cell death, while others exhibit subtle phenotypes that are barely perceivable, such as changes in morphology or distribution of subcellular structures (i.e. nuclei, cytoskeleton, mitochondria, etc.), and some exhibit no change at all. A multi-class network may not be able to properly learn subtle phenotypes.

In an exemplary embodiment of the subject technology, a series of 2-class neural network training steps may be used, where a separate model is created for each drug dose compared to its control. As will be appreciated, a high level of sensitivity in detecting structural changes will be generated. As a result, aspects of the subject technology successfully capture obvious phenotypes, such as cell damage and death, as well as subtle phenotypes, such as changes to sarcomere organization or distribution of mitochondria.

As detailed in the following sections, the input imaging data is processed and may be augmented before training deep neural networks. For each test condition, images from a well are dedicated for validation and the rest are used for training. The performance of each training may be used on the validation wells as the measure of structural change. If the accuracy of the trained neural network for dose i is low, it means that the neural network was not able to reliably detect any difference between the drug-dose i-treated and reference (vehicle) images and hence no structural change was detected. One the other hand, if the achieved accuracy is high, it means that the trained neural network was able to differentiate between the drug-treated images at dose i versus the vehicle images, and the strength of the change is calculated from the distribution of class probabilities.

Figure 1:
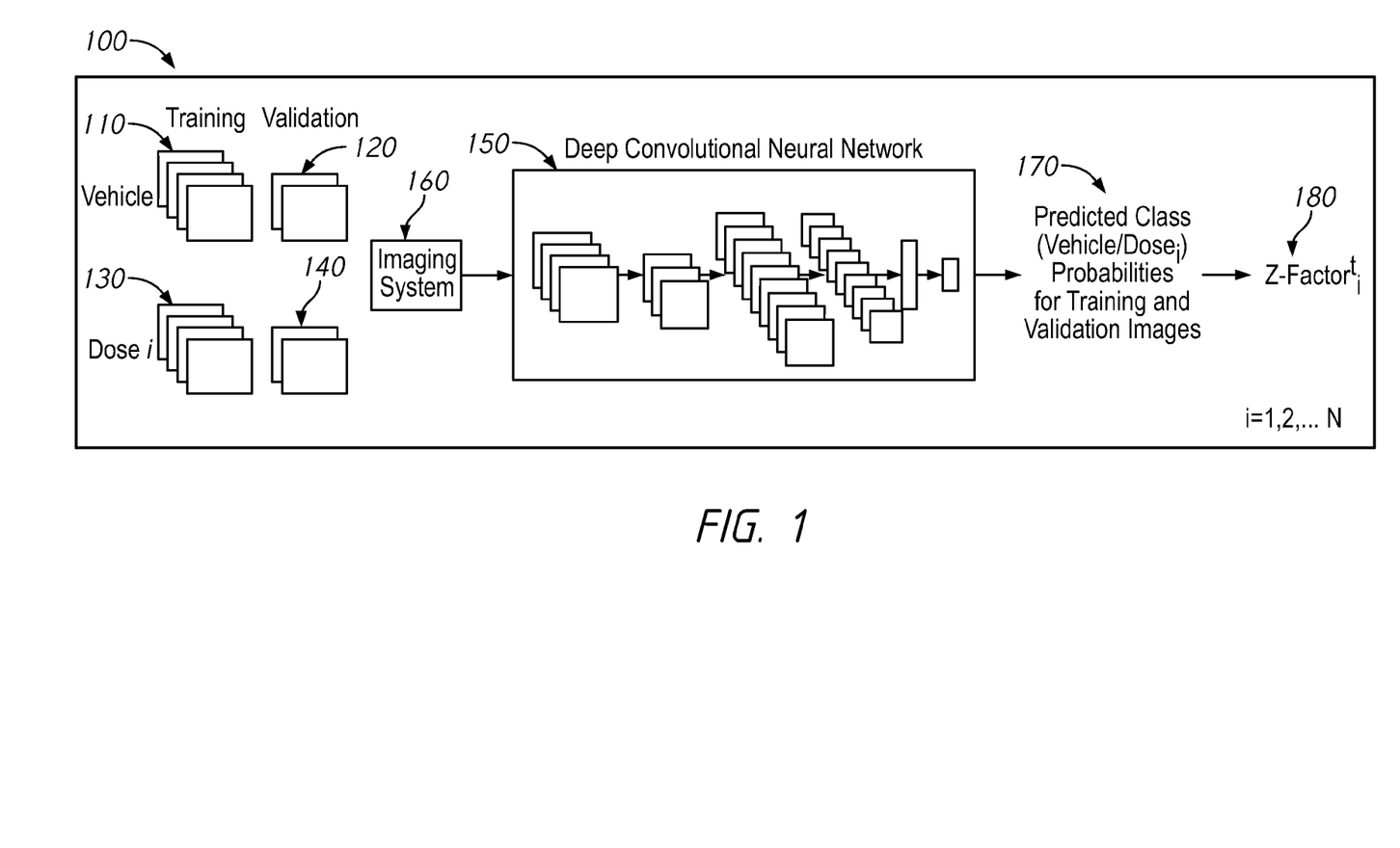
FIG. 1 is a system for testing structural toxicity in cells from drugs in accordance with an exemplary embodiment of the subject technology.

Referring now to FIG. 1, a system 100 (referred to generally as the "system 100") for testing structural toxicity in cells from drugs is shown according to an exemplary embodiment. The system 100 includes an artificial intelligence (AI) module 150 that is configured to receive images of cell cultures that are dosed with drugs so that AI module 150 may analyze the images for structural changes in the cells. The AI module 150 learn from the images what changes may demonstrate a significant structural change that may indicate toxicity to a drug. In an exemplary embodiment, the AI module 150 may be a deep convolutional neural network (CNN). An imaging system 160 may be connected to the AI module 150. Images of training and validation cultures may be taken by the imaging system 160 and electronically forwarded to the AI module 150. The cultures may comprise vehicle training culture images 110 and vehicle validation cultures 120. The cultures may also comprise dosage training culture images 130 and dosage validation culture images 140. The images (110, 120, 130, and 140) may be processed by the AI module 150 to generate output 170. The output result of the analysis may be for example, a set of classification results, such as accuracies or z-factors 180, that quantify the degree of structural changes that have occurred at each dose for the drug(s) of interest.

Figure 2:
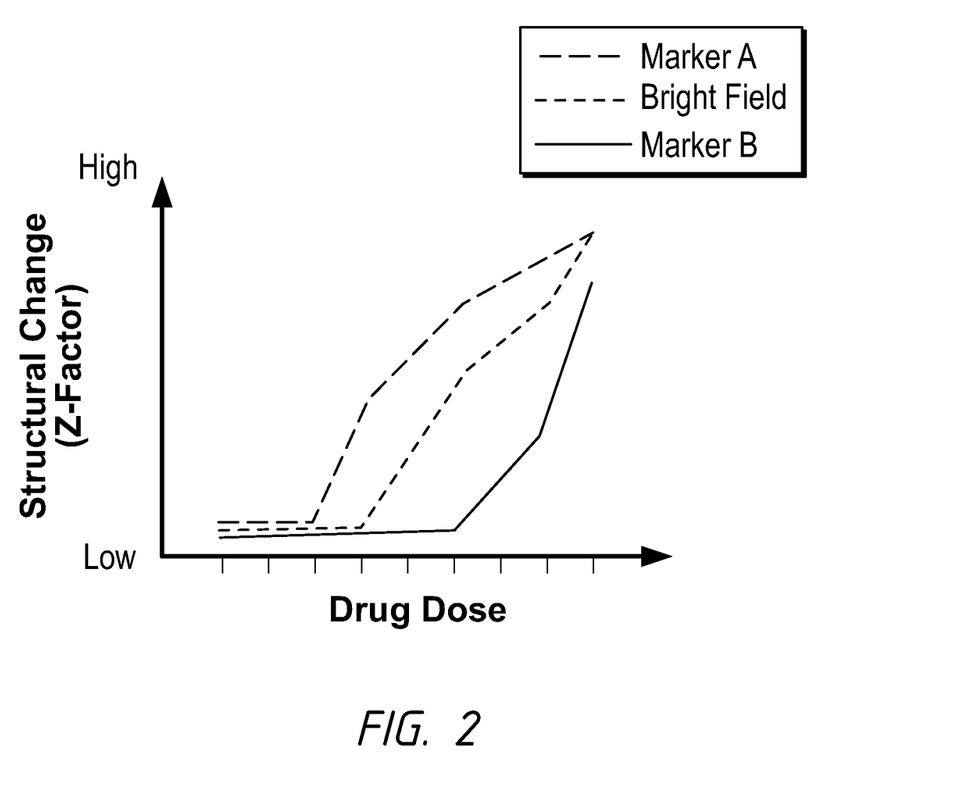
FIG. 2 is a plot comparing structural changes of cells based on drug dosage level results determined by the system of FIG. 1 for a plurality of image channels in accordance with an exemplary embodiment of the subject technology.

FIG. 2 shows a plot as an example result of the analysis by the system 100 of FIG. 1 for three different image channels. The plot shows how an increasing level of drug dosage may generally affect the structural change in subject cells under observation. The AI part of the system may use the different performances under different image channels to generate insights into which cellular structures are being affected by the drug.

Figure 3:
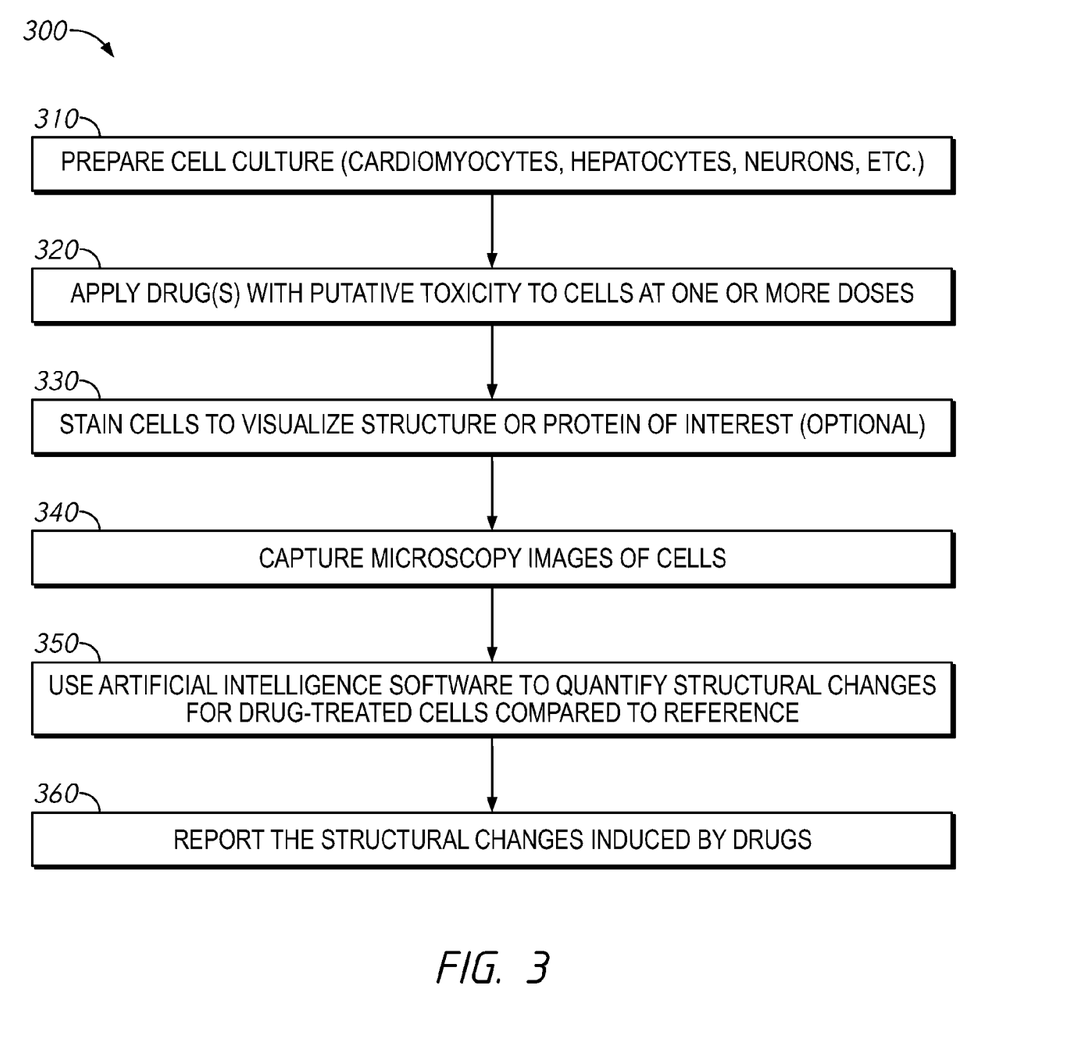
FIG. 3 is a flowchart of a method of determining structural effects of drugs to cells in accordance with an exemplary embodiment of the subject technology.
Figure 4:
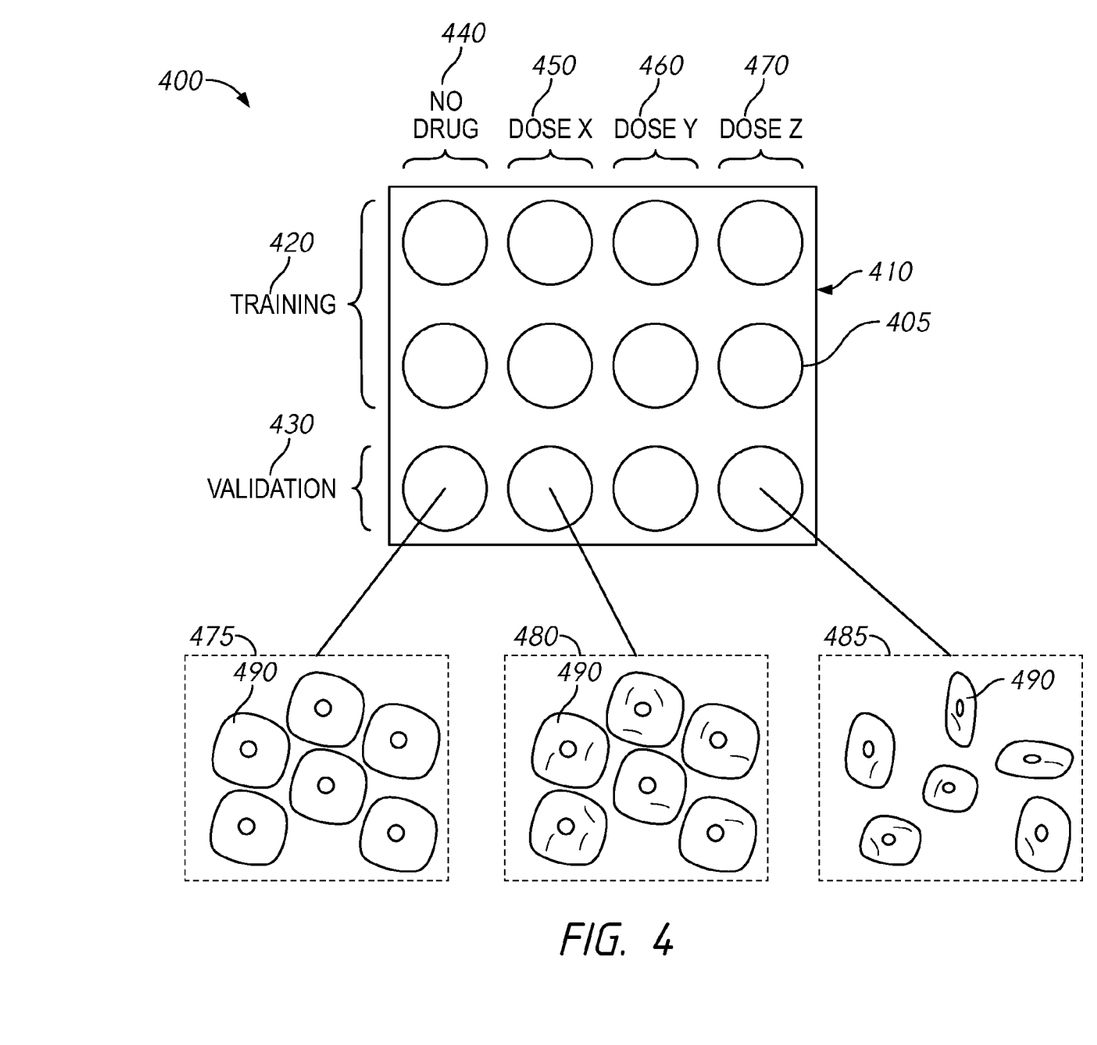
FIG. 4 is a diagrammatic view of an experimental setup for culturing cells and applying drugs in accordance with an exemplary embodiment of the subject technology.

In the following disclosure, FIGS. 3 and 4 may be referenced simultaneously. FIG. 1 shows a method 300 of determining structural effects of drugs to cells according to an exemplary embodiment. In an exemplary application, the method 300 may be used in an in vitro phenotypic assay setup. FIG. 4 shows an example in vitro phenotypic assay setup 400 so that one may visualize the method as applied to a cell culture plate 410. Elements in the method 300 will be made using reference numerals in parentheses. References to non-method elements will be made using numerals without parentheses.

The setup may include preparing (310) one or more cell culture plates 410 of wells 405. In this example a single drug is being tested. The first column 440 of wells 405 has no drug applied, which serves as a reference. The second column 450 of wells has the drug applied at dose X, the third column 460 of wells has drug applied at dose Y, and the fourth column 470 of wells has the drug applied at dose Z. The first two rows 420 of wells may be used for training data for the CNN, and the third row 430 of wells may be used for validation data for the CNNs.

While only a dozen cultures are shown, it will be appreciated that one of the benefits of an automated system using AI in this context is that several dozen cultures (or more) may be subjected to a test and monitored over time by the machine elements of the subject technology. The plates 410 can be a multi-well format such as a 6, 12, 24, 48, 96, or 384-well plate. The cells 490 may be primary or iPSC-derived cardiomyocytes, hepatocytes, neurons, cancer cells, immune cells, reproductive cells, or any other cell type of-interest.

Some embodiments may test one or more drugs of different types with putative toxicity that are applied (320) to the cells 490 at one or more doses. As shown, only a single drug is being observed for toxicity compared to cells that are not treated with any drug or only the drug vehicle (for example, DMSO) applied, to serve as a reference.

In some embodiments, the cells 490 under observation may be stained (330) to visualize a structure or protein of interest. The cells 490 can be fixed as part of the staining, or a live-cell stain may be used. For example, reagents can be used to label nuclei, actin fibers (or other elements of the cytoskeleton), mitochondria, or any other cell component. A combination of stains can also be used.

Next, images of the cells 490 are captured (340). In an exemplary embodiment, a microscope may be used to capture the images. The images may be acquired at multiple spots per well 405, to increase the amount of image data. In FIG. 4, images 475,480, and 485 are enlarged views of some of the captured images of the cells 490 under test. Image 475 shows a cell culture without any drug applied to the culture. Image 480 shows a cell culture with a first dosage ("Drug Dose X") of a drug applied to the cells. Image 485 shows a cell culture with a second dosage ("Drug Dose Z") of a drug applied to the cells. The second dosage may not be of the same strength as the first dosage. While a drug dosage "Y" is shown, images for this dosage are not shown for sake of illustration. As shown in the example of FIG. 4, the drug being observed may affect the cells' structures in varying degrees of structural changes depending on the dosage applied. The cells 490 in the no-drug column 440 (image 475) show normal morphology and structure. The cells 490 in the dose X column 450 (image 480) show slight changes. The cells 490 in the dose Z column (image 380) show significant changes and potentially cell death.

Fluorescence microscopy may be used for stained cells, while transmitted light microscopy (for example, brightfield, phase contrast, DIC) may be used for unstained cells. In order to capture many images efficiently, the microscope may be part of a high-content or high-throughput imaging system. The images may be single-channel images, or multi-channel images, such as red-green-blue (RGB) images. When using multi-channel images, the channels may include brightfield images, and fluorescence images captured at different wavelengths in order to visualize different cellular structures. As one example of an experimental setup, the cells are iPSC-derived hepatocytes, the drug under investigation is tamoxifen (a drug with known liver toxicity), dose X is 0.01 uM, dose Y is 0.10 uM, dose Z is 1.00 uM, the cells are fixed and stained with phalloidin-conjugated fluorescent dyes, and the imaging is performed with an inverted fluorescence microscopy system, capturing multiple images at each individual well.

Once the images are captured, an artificial intelligence process(es) is applied (350) to quantify the structural changes. A series of 2-class CNN trainings may be performed, comparing each drug condition to a reference point.

These results are reported (360) to the user for subsequent visualization.

Figure 5:
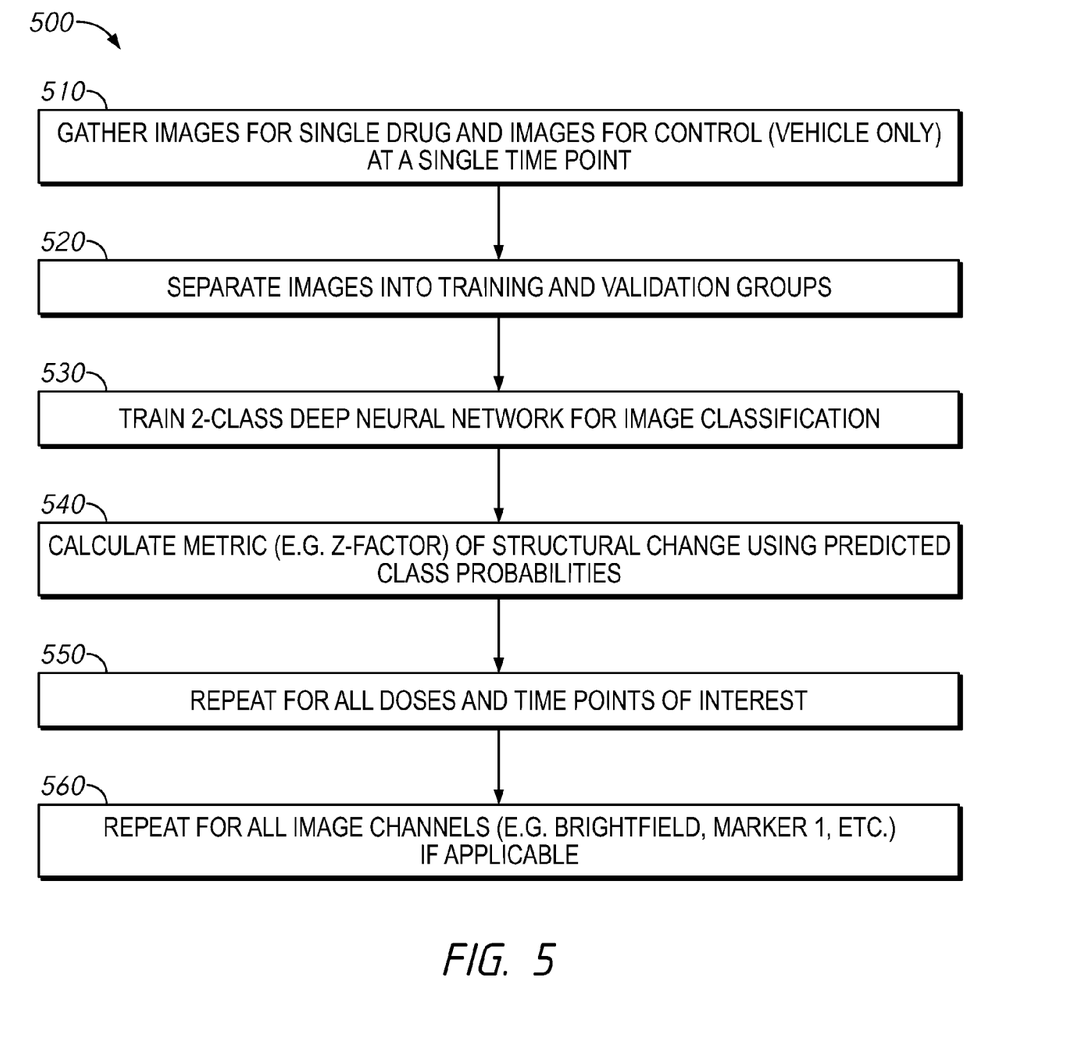
FIG. 5 is a flowchart of an artificial intelligence process of quantifying structural effects of drugs to cells in accordance with an exemplary embodiment of the subject technology.

Referring now to FIG. 5, an artificial intelligence process 500 (referred to generally as the "process 500") of quantifying structural effects of drugs to cells is shown according to an exemplary embodiment. In some embodiments, the process 500 may be a sub-process of the step (350) shown in FIG. 3 and may be a method embodiment of the events occurring in block 150 of FIG. 1. It should be understood that the steps in process 500 may be machine implemented (for example, by a computing device or other electronic device) unless otherwise noted.

Images for a single drug and images for a control may be gathered (510) at a single point in time. The gathered images may be separated (520) into training and validation groups.

In some embodiments, millions of images may be already used to pre-train the CNN from a third-party source such as ImageNet database. In some embodiments of the training process, the weights of the neural network may be initialized by the pre-trained network. The first layers may be frozen (which encode the low-level features such as edge detection and are less application dependent).

Since microscopy images typically have higher resolution (larger number of pixels) than what neural networks train on, the images can optionally be divided into sub-images, or patches, prior to training. The original images can be divided into patches using a grid (for example, 2×2, 3×3, 4×3, or other) or by first segmenting for cell foreground and then creating patches around the segmented regions. The CNN performance can be measured on the individual patches, or the performance can be measured on the whole-image level using an aggregated set of results from all patches within each image.

A 2-class deep neural network may be trained (530) for image classification. The higher layers of the neural network may be allowed to learn the image features. The training may be performed with an initial learning rate of 0.01 for 20 epochs and may be repeated three times. For each training session, the final neural network may be selected from the epoch with the highest validation accuracy.

To generate the input data to train the neural network, each image may be processed and augmented. A series of 2-class deep convolutional neural network trainings comparing images of each test condition (drug dose i {1:N} to vehicle-only data (FIG. 1), where N is the total number of doses being tested at a single timepoint. The input imaging data can be for example, florescence images of fixed and stained cells or live-cell brightfield images. The system may determine whether images of cells treated with a drug dose are different from images of cells treated with vehicle only, and if so, how strongly they differ. The insight as to which cellular features are showing structural change comes from collecting images and training separate models on different structures and proteins such as actin, mitochondria, nucleus, calcium, membrane-associated proteins, and others.

Prior to training, the images or image patches can be augmented in order to increase the amount of data and add variability to the dataset. Each image may be partitioned into nonoverlapping square sub-images. Each sub-image may go through a combination of flipping and rotation at 90, 180, and 270 degrees to create a set of 8 augmented sub-images. Image augmentation may also include shifting images, adding noise, or any other augmentation process.

As may be appreciated, the input training dataset may thus be placed in the right resolution and to increase the sample size for improved performance. The fact that rigid transformations do not affect the class labels of cellular images may be leveraged. The total number of generated data for an example experiment may be 6 wells for each drug dose, 9 images per well, and 96 sub-images per well, yielding a total of 5184 sub-images per drug dose (or control), creating a total of 10368 images of 300×300 pixels for the deep neural network training.

A metric of structural change in the images of the cells may be calculated (540). In an exemplary embodiment, the metric may be a Z-factor measure. In an exemplary embodiment, the metric calculated may be performed by using predicted class probabilities on the image data. The performance metrics for each model may be the classification accuracy for both the training images and validation images, in addition to class probabilities per image. Defining a metric of structural change may be based on the Z-factor calculated over the image-level probabilities in the validation set, as well as training and validation accuracies. In an exemplary embodiment, the metric of structural change, Z-Factor' is defined as:

$$\text{Z-Factor}' = \begin{cases} Z\ Factor, & Z\ Factor > -1\ and\ _{Training}\ Accuracy \geq 90\%\ and\ Validation\ Accuracy \geq 75\% \\ -1 & , \quad else \end{cases}$$

If the accuracy of the trained neural network is low (<90% for training, <75% for the validation, or validation ZFactor <-1), it means that the neural network was not able to reliably detect any difference between the drug-treated and reference images, hence no structural change detected. If the neural network has achieved high accuracy on both the training and validation set (for example, ≥90% for training and ≥75% for validation), then it means that the trained neural network was able to differentiate between the drug-treated images and vehicle-only images in the validation wells, and the calculated Z-factor value then denotes the strength of the change. The output of the system includes the performance metrics for all trainings and the final Z-Factor' on the validation set in the range of -1 to 1 as the measure of structural change.

The performance of neural networks for the task of image classification can be defined in numerous ways beyond classification accuracy. In another embodiment, the interpretable measure may use Tjur's pseudo $R^2$, which includes the difference between the average of predicted class probabilities. The metric of structural change may be based on the Tjur's pseudo $R^2$ calculated over the probabilities, which is the distance between the mean of class probabilities in the validation set, as well as training and validation classification accuracies:

Structural Change=
$$\begin{cases} Tjur's\ pseudo\ R2, & if\ _{Training} Accuracy => 90\%\ and\ Validation\ Accuracy => 75\% \\ 0 & , \qquad otherwise \end{cases}$$

Blocks 510-540 may be repeated (550) for all doses being analyzed and for all points in time of interest. In some embodiments, blocks 510-550 may be repeated for all image channels.

Figure 6:
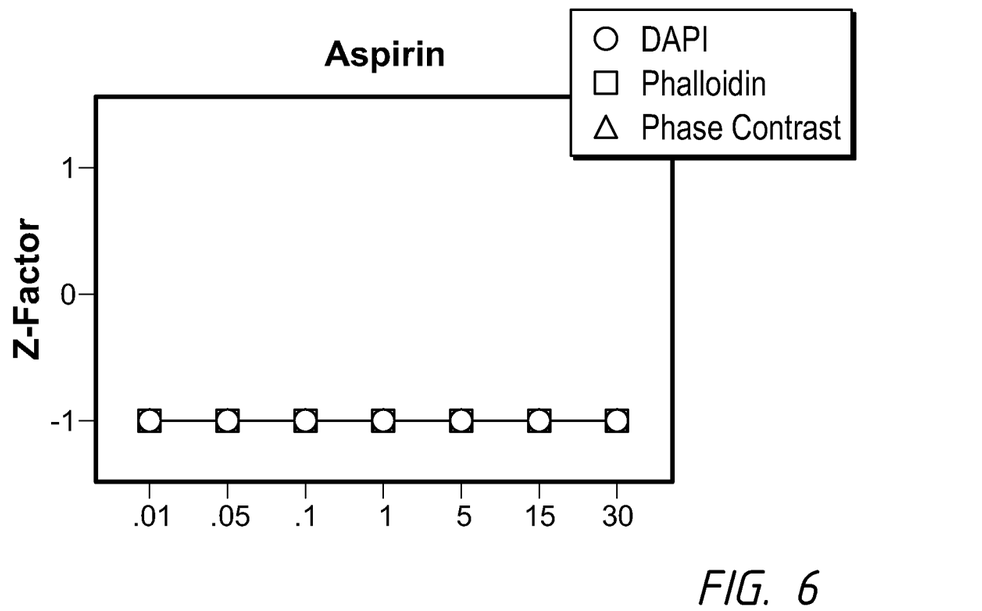
FIG. 6 is a plot displaying the results of structural damage on liver cells by aspirin captured by embodiments of the subject technology.

Referring now to FIG. 6, a plot showing the results of the subject technology observing the effects of aspirin to cells is shown. As can be seen, the drug causes no, or minimal, structural changes in the cells. As another example, the drug under investigation is a newly developed drug with unknown toxicity profile, and the goal of the experiment is to see what, if any, structural changes are caused.

Figure 7:
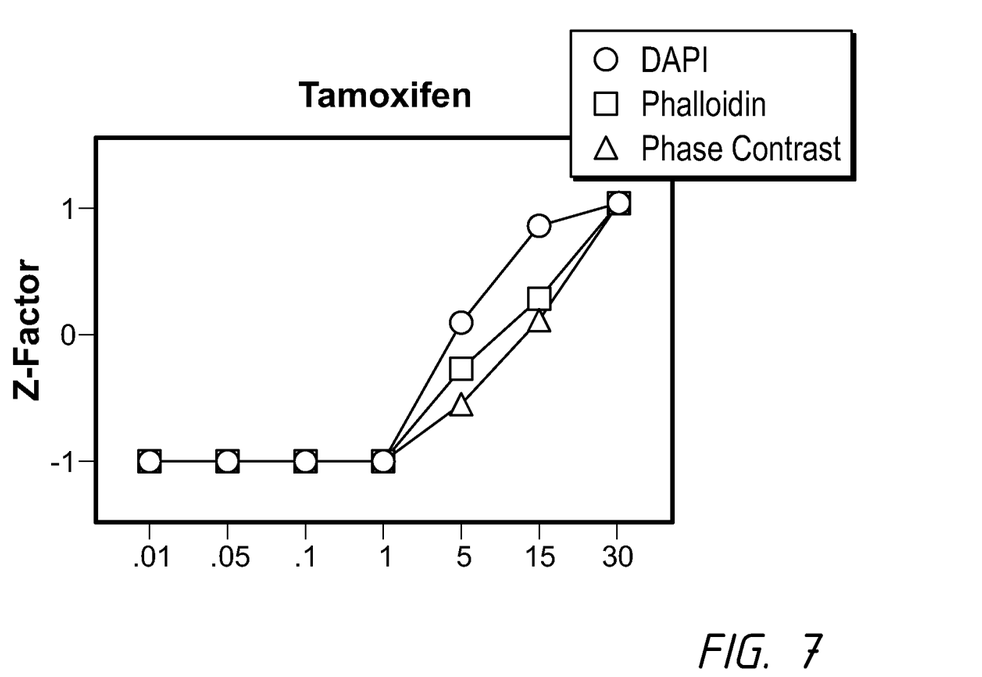
FIG. 7 is a plot displaying the results of structural damage on liver cells by tamoxifen captured by embodiments of the subject technology.

FIG. 7 shows another example of results derived by aspects of the subject technology. The cells are iPSC-derived hepatocytes, the drug under investigation is tamoxifen, the reference images are from one or more wells with only the vehicle (DMSO) applied, and the drug-treated cells are from one or more wells with multiple doses of 0.01 uM, 0.05 uM, 0.1 uM, 1.00 uM, 5 uM, 15 uM, and 30 uM applied. The images were divided into a grid of 5×4 patches, and the patches were augmented. The CNN architecture is an 18-layer residual network, the image patches are resized to 224×224 pixels, the learning rate is 0.01, and the trainings are run for 20 epochs. The validation z-factors show values above -1 starting at a dose of 5 uM, indicating of the start of structural changes between drug-treated cells and reference cells.

Figure 8:
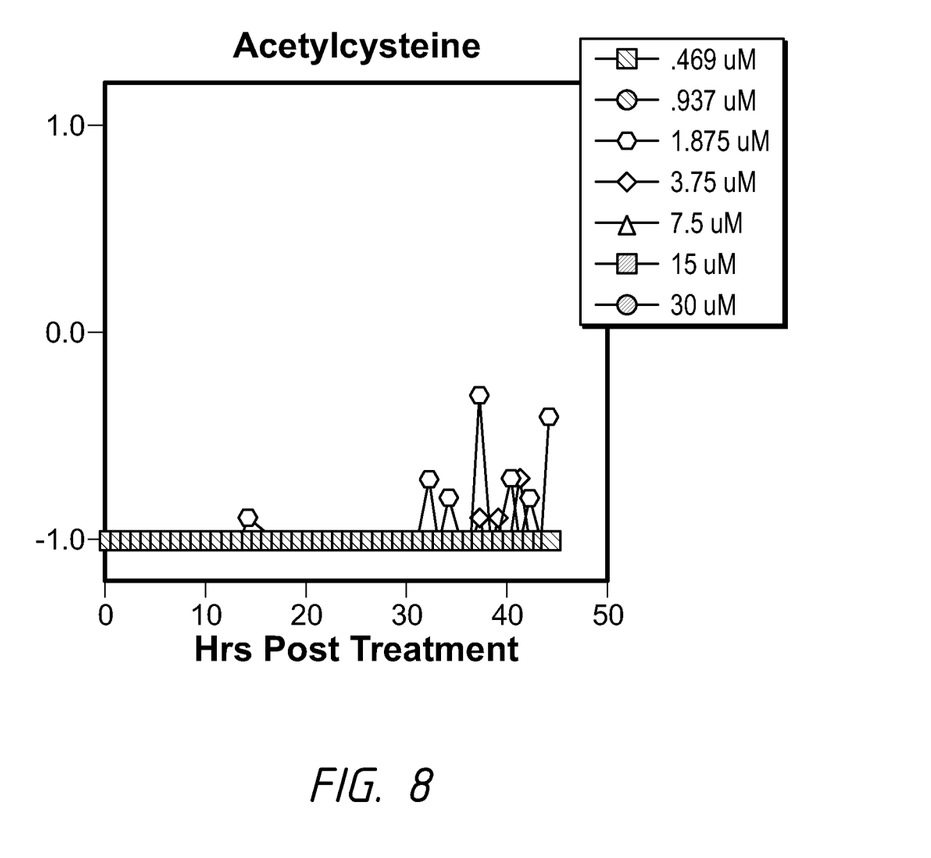
FIG. 8 is a plot displaying levels of structural damage on cells over time by acetylcysteine captured by embodiments of the subject technology.
Figure 9:
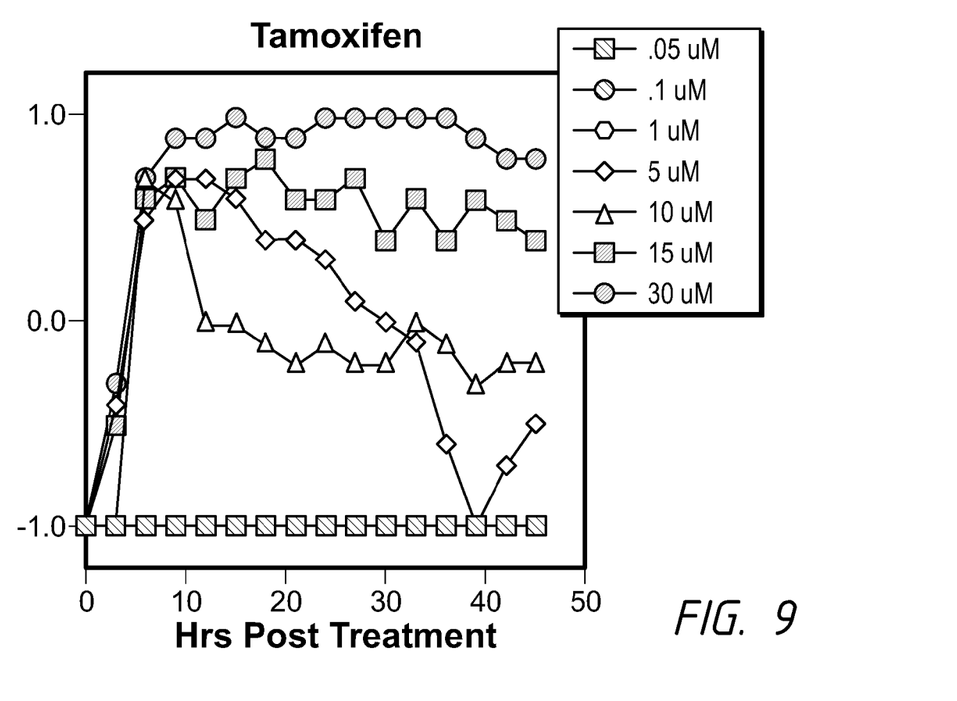
FIG. 9 is a plot displaying levels of structural damage on cells over time by tamoxifen captured by embodiments of the subject technology.
Figure 10:
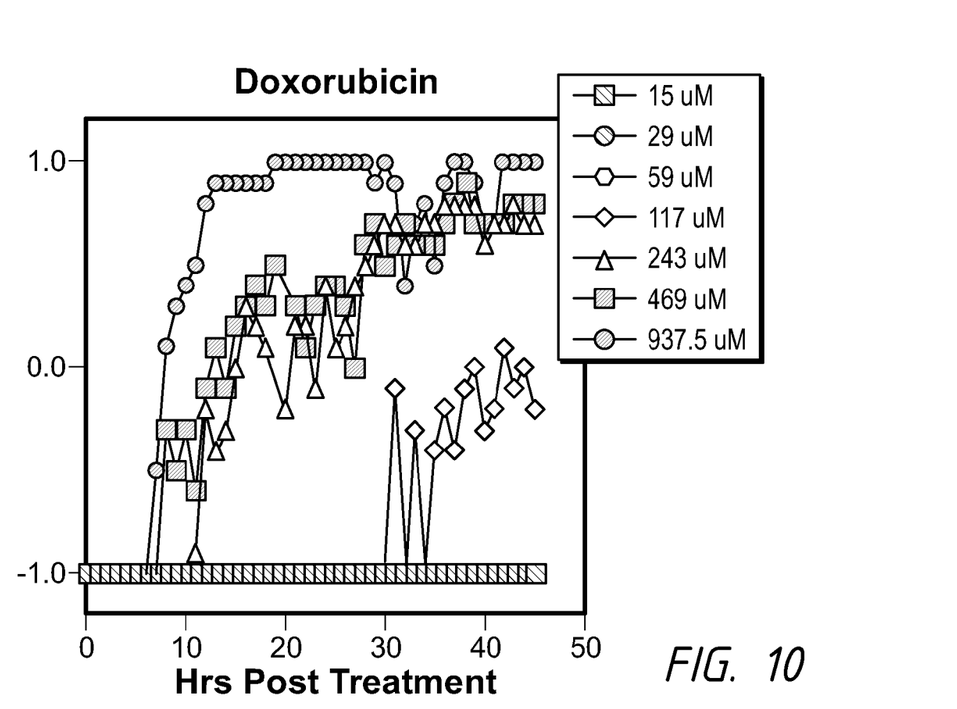
FIG. 10 is a plot displaying levels of structural damage on cells over time by doxorubicin captured by embodiments of the subject technology.

FIGS. 8-10 show plots of results showing the structural damage of liver cells when subjected to three different drugs over time. FIG. 8 shows the results of acetylcysteine, which as would be expected, show little damage to the cells throughout 48 hours of exposure. FIG. 9 shows that the system not only detects noticeable structural damage from exposure to tamoxifen, but that different dosage amounts may cause different levels of structural damage over time. FIG. 10 shows the effects of doxorubicin on the cells. The system also detects changes in the structural integrity of the cells. In addition, the dosage amount may result in differences in how much damage may be caused over time which is also valuable information.

In other applications, the reference can be images of cell cultures treated with other drugs and/or doses. For example, a 2-class CNN may be trained to compare a drug at dose X against the same drug at dose Y. Or a 2-class CNN may be trained to compare drug A against drug B at the same doses. In these types of applications, a series of different combinations can be investigated to determine how a drug compares to other drugs in terms of their induced structural changes on the cells.

The artificial intelligence module 150 may consist of other types of 2-class neural networks besides convolutional neural networks. The artificial intelligence module 150 may also include multi-class neural networks where, for example, the classes include a reference, a drug-treated cell culture, and background (where little or no cells are visible). Other types of neural networks such as autoencoders may also be used. The type of neural network, the definition of classes, and the number of classes depends on the type of toxicity testing and/or the structural element under testing. The artificial intelligence module 150 may also include classes or separate trained neural networks for identification of poor-quality images, such as out-of-focus images, to provide a means of quality control.

The output of the subject technology is a set of classification results, such as validation accuracies and/or z-factors, that quantify the degree of structural changes. These outputs can be combined or supplemented with other analysis outputs such as image quality, cell foreground and/or background (which may provide an indirect measure of cell death), cell segmentation results, or any other metric. The output measures can be displayed separately or combined, and can be given weightings based on their importance.

Figure 11:
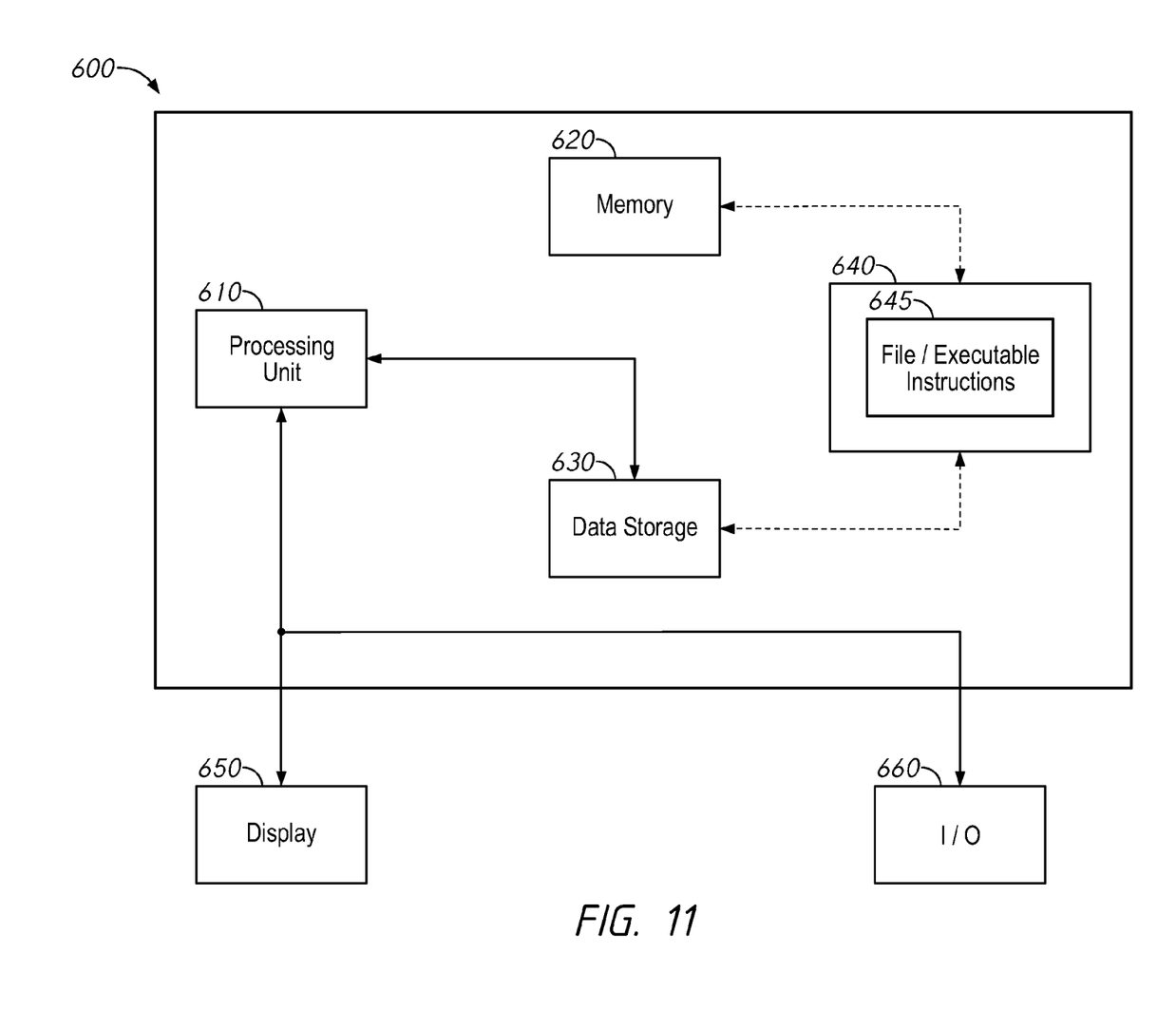
FIG. 11 is a block diagram of a general computing device used to apply artificial intelligence aspects of embodiments of the subject technology.

Referring now to FIG. 11, a computing device 600 is shown according to an exemplary embodiment. The computing device 600 generally represents a machine performing functions related to the artificial intelligence aspects discussed above. The computing device 600 may be for example, a computer system, a computer server, or a group of computers networked together to process the images of the cells gathered. As will be appreciated, some aspects of the embodiments disclosed above may turn the computing device 600 into a special purpose computer system for determining in vitro structural toxicity of drugs on cells.

In some embodiments, the computing device 600 may be a user device accessed by users to review the results. In the role of a user device, the computing device 600 is generally not a server but may instead be desktop computers, tablet or laptop computers, all-in-one computer stations, a mobile computing device (for example, a smart phone, smart wearable devices (glasses, jewelry, watches, ear wear, etc.), or programmable electronics.

The components of the computing device 600, may include, but are not limited to, one or more processors or processing units 610, a system memory 620, data storage 630, a computer program product 640 having a set of program modules 645 including files and executable instructions, and a bus system that couples various system components including the system memory 620 to the processor(s) 610. The memory storage 620 may store for example, captured images, training sets of images, training data, calculated metrics, determinations of structural damage to cells under test, and processes for determining the general toxicity of drugs on cells. In some embodiments, the processors 610 may include a processing unit dedicated to graphics and image processing (for example a graphics processing unit (GPU) or visual processing unit (VPU). As a GPU or VPU, the processor 610 may implement executable instructions focused on image processing applications either alone or in coordination with other general processor 610 types such a CPUs, microchips, and the like to recognize the features in cell images and in some embodiments, detect structural damage.

The computing device 600 may be described in the general context of computer system executable instructions, such as the program modules 645 which represent a software embodiment of the system and processes described generally above. The program modules 645 generally carry out the functions and/or methodologies of embodiments as described above. The computing device 600 may typically include a variety of computer system readable media. Such media could be chosen from any available media that is accessible by the computing device 600, including non-transitory, volatile and non-volatile media, removable and non-removable media for use by or in connection with an instruction execution system, apparatus, or device. A computer readable storage medium may be, for example, but not limited to, an electronic, magnetic, optical, electromagnetic, infrared, or semiconductor system, apparatus, or device, or any suitable combination of the foregoing. The system memory 620 could include one or more computer system readable media in the form of volatile memory, such as a random-access memory (RAM) and/or a cache memory. By way of example only, the data storage system 630 may read from and write to a non-removable, non-volatile magnetic media device. The system memory 620 may include at least one program product 640 having a set (e.g., at least one) of program modules 645 that are configured to carry out the functions of embodiments of the invention in the form of computer executable instructions. The program product/utility 640, having a set (at least one) of program modules 645, may be stored in the system memory 620 by way of example, and not limitation, as an operating system, one or more application programs, other program modules, and program data.

The computing device 600 may communicate with one or more external devices including for example, an electronic display 650 which may in some embodiments be configured for tactile response as in a touch screen display. User input into the display 650 may be registered at the processor 610 and processed accordingly. Other devices may enable the computing device 600 to communicate with one or more other computing devices, either by hardwire or wirelessly. Such communication can occur via Input/Output (I/O) interfaces/ports 660. In some embodiments, the I/O interfaces/ports 660 may be specially configured to handle aspects of the embodiments described herein converting the computing device 600 into a special purpose machine. The computing device 600, through the I/O interface/ports 660, may communicate with one or more networks such as a local area network (LAN), a general wide area network (WAN), and/or a public network (e.g., the Internet) via a network adapter as is commonly known in the art. Each of the operating system, one or more application programs, other program modules, and program data or some combination thereof, may include an implementation of a networking environment. In some embodiments, the computing device 600 may be a cloud computing node connected to a cloud computing network (not shown). The computing device 600 may be practiced in distributed cloud computing environments where tasks are performed by remote processing devices that are linked through a communications network. In a distributed cloud computing environment, program modules may be located in both local and remote computer system storage media including memory storage devices.

As will be appreciated by one skilled in the art, aspects of the disclosed invention may be embodied as a system, method or process, or computer program product. Accordingly, aspects of the disclosed invention may take the form of an entirely hardware embodiment, an entirely software embodiment (including firmware, resident software, microcode, etc.) or an embodiment combining software and hardware aspects that may all generally be referred to herein as a "module", "circuit", or "system." Furthermore, aspects of the disclosed invention may take the form of a computer program product embodied in one or more computer readable media having computer readable program code embodied thereon. In some embodiments, the output of the computer program product provides an electronic user interface on the display 650 which may be controlled via direct contact with the display 650 or via the I/O interfaces 660 (which may be for example, interface devices such as keyboards, touchpads, a mouse, a stylus, or the like).

Aspects of the disclosed invention are described above with reference to block diagrams of methods, apparatus (systems) and computer program products according to embodiments of the invention. It will be understood that each block of the block diagrams, and combinations of blocks in the flowchart illustrations and/or block diagrams, can be implemented by computer program instructions. These computer program instructions may be provided to the processor 610 of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks in the figures.

Those of skill in the art would appreciate that various components and blocks may be arranged differently (e.g., arranged in a different order, or partitioned in a different way) all without departing from the scope of the subject technology. The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects.

Thus, the claims are not intended to be limited to the aspects shown herein, but are to be accorded the full scope consistent with the language of claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

Persons of ordinary skill in the art may appreciate that numerous design configurations may be possible to enjoy the functional benefits of the inventive systems. Thus, given the wide variety of configurations and arrangements of embodiments of the present invention the scope of the present invention is reflected by the breadth of the claims below rather than narrowed by the embodiments described above.

What is claimed is:

1. A computer program product to determine a response of a cell to a drug, the computer program product comprising a non-transitory computer readable storage medium having computer readable program code embodied therewith, the computer readable program code being configured, when executed by a processor, to:
   receive images of treated cells, wherein the treated cells are exposed to the drug, at an initial point in time;
   receive images of control cells not exposed to the drug;
   forward the images of the treated cells and the images of the control cells to a convolutional neural network;
   determine by the convolutional neural network whether the images of the treated cells are different from the images of the control cells; and
   calculate a metric based on the determination by the convolutional neural network quantifying an amount of change caused by the drug on the treated cells.

2. The computer program product of claim 1, further comprising computer readable program code configured to:
   wherein the treated cells are exposed to multiple dosages of the drug and the determination is by a series of convolutional neural networks and includes quantifying changes associated with each of the multiple dosages.

3. The computer program product of claim 1, wherein the treated cells are exposed to multiple types of drugs and the determination is by a series of convolutional neural networks and includes quantifying changes associated with each of the multiple types of drugs.

4. The computer program product of claim 1, wherein the determination is by a series of convolutional neural networks and includes quantifying changes at multiple points in time after the initial point in time.

5. The computer program product of claim 1, wherein:
   the received images of the treated cells and the received images of the control cells are received on multiple image channel types; and
   the determination is by a series of convolutional neural networks and includes quantifying changes shown in each channel type.

6. The computer program product of claim 1, wherein the metric calculated is a z-factor measure.

7. The computer program product of claim 1, wherein the convolutional neural network uses a 2-class classification basis.

8. The computer program product of claim 1, wherein the metric calculated is Tjur's pseudo R2.

9. A method for determining an automated response of a cell to a drug, comprising:
   receiving images of treated cells, wherein treated cells are exposed to the drug, at an initial point in time;
   receiving images of control cells not exposed to the drug;
   forwarding the images of the treated cells and the images of the control cells to a convolutional neural network;
   determining by the convolutional neural network whether the images of the treated cells are different from the images of the control cells; and
   calculating a metric based on the determination by the convolutional neural network quantifying an amount of change caused by the drug on the treated cells.

10. The method of claim 9, wherein the treated cells are exposed to multiple dosages of the drug and the determination is by a series of convolutional neural networks includes and quantifying changes associated with each of the multiple dosages.

11. The method of claim 9, wherein the treated cells are exposed to multiple types of drugs and the determination is by a series of convolutional neural networks and includes quantifying changes associated with each of the multiple types of drugs.

12. The method of claim 9, wherein the determination is by a series of convolutional neural networks and includes quantifying changes at multiple points in time after the initial point in time.

13. The method of claim 9, wherein:
   the received images of the treated cells and the received images of the control cells are received on multiple image channel types; and
   the determination is by a series of convolutional neural networks and includes quantifying changes shown in each channel type.

14. The method of claim 9, wherein the metric calculated is a z-factor measure.

15. The method of claim 9, wherein the convolutional neural network uses a 2-class classification basis.

16. The method of claim 9, wherein the metric calculated is Tjur's pseudo R2.

* * * * *